(12) United States Patent
Daugherty et al.

(10) Patent No.: US 7,007,691 B2
(45) Date of Patent: Mar. 7, 2006

(54) APPARATUS AND METHOD FOR HUMIDIFICATION OF INSPIRED GASES

(76) Inventors: Roger Daugherty, 1085 Druid Lake, Decatur, GA (US) 30033; Derrick Wilson, 273 Stovall Rd., LaGrange, GA (US) 30241

( * ) Notice: Subject to any disclaimer, the term of this patent is extended or adjusted under 35 U.S.C. 154(b) by 0 days.

(21) Appl. No.: 10/669,108

(22) Filed: Sep. 23, 2003

(65) Prior Publication Data

US 2004/0226559 A1 Nov. 18, 2004

Related U.S. Application Data

(63) Continuation-in-part of application No. 10/436,535, filed on May 13, 2003.

(51) Int. Cl.
*A61M 15/00* (2006.01)
*A61M 15/08* (2006.01)
*A61M 16/00* (2006.01)
*A62B 9/02* (2006.01)

(52) U.S. Cl. .......................... 128/203.12; 128/204.18; 128/204.24; 128/204.26; 128/204.28; 128/205.24; 128/203.16; 128/205.19; 128/205.12; 128/202.27

(58) Field of Classification Search ................ 128/911, 128/912, 204.18, 204.24, 204.26, 204.28, 128/205.24, 203.16, 205.19, 205.12, 203.12, 128/202.27
See application file for complete search history.

(56) References Cited

U.S. PATENT DOCUMENTS

| | | | |
|---|---|---|---|
| 3,713,440 A | * | 1/1973 | Nicholes ................ 128/205.12 |
| 3,756,244 A | | 9/1973 | Kinnear et al. |
| 3,856,051 A | | 12/1974 | Bain |
| 3,865,106 A | | 2/1975 | Palush |
| 3,945,378 A | | 3/1976 | Paluch |
| 3,995,625 A | * | 12/1976 | Needham ................ 128/204.26 |
| 4,007,737 A | | 2/1977 | Paluch |
| 4,188,946 A | | 2/1980 | Watson et al. |
| 4,265,235 A | * | 5/1981 | Fukunaga ................ 128/200.24 |
| 4,320,754 A | | 3/1982 | Watson et al. |
| 4,462,397 A | | 7/1984 | Suzuki |
| 4,463,755 A | | 8/1984 | Suzuki |
| 4,621,634 A | * | 11/1986 | Nowacki et al. ....... 128/204.18 |
| 4,637,384 A | * | 1/1987 | Schroeder .............. 128/204.18 |
| 4,686,354 A | * | 8/1987 | Makin ........................ 392/472 |
| 4,967,744 A | * | 11/1990 | Chua ....................... 128/204.18 |
| 5,121,746 A | * | 6/1992 | Sikora ..................... 128/203.12 |
| 5,284,160 A | * | 2/1994 | Dryden ................... 128/203.12 |

(Continued)

FOREIGN PATENT DOCUMENTS

CA 1133350 10/1982

(Continued)

*Primary Examiner*—Henry Bennett
*Assistant Examiner*—Nihir Patel
(74) *Attorney, Agent, or Firm*—Ashish D. Patel, Esq.; Joel D. Myers, Esq.; Myers & Kaplan, LLC

(57) ABSTRACT

An apparatus and method for humidification of inspired gases, wherein the present invention utilizes moisture from condensed expiratory gases deposited within the outer expiratory tube of a conventional unilimb breathing circuit to humidify oxygen gas (or any other inspiratory gas) for subsequent patient inhalation, and wherein the oxygen gas may be directed through the outer expiratory tube via a novel reverse flow adapter coupled to an oxygen gas source. The present invention preferably functions to effectively eliminate prior art methods of oxygen gas humidification that depend upon the wasteful utilization of bottles of sterile water, corrugated tubing, nebulizer adapters and excess consumption of oxygen gas; thus, effectuating a cost savings for the patient and contributing to overall environmental conservation efforts.

11 Claims, 7 Drawing Sheets

U.S. PATENT DOCUMENTS

| | | | | |
|---|---|---|---|---|
| 5,404,873 | A * | 4/1995 | Leagre et al. | 128/204.18 |
| 5,640,951 | A * | 6/1997 | Huddart et al. | 128/204.17 |
| 5,778,872 | A * | 7/1998 | Fukunaga et al. | 128/202.27 |
| 5,823,184 | A | 10/1998 | Gross | |
| 5,894,839 | A * | 4/1999 | Rosenkoetter et al. | 128/200.24 |
| 5,901,705 | A * | 5/1999 | Leagre | 128/207.14 |
| 5,983,894 | A | 11/1999 | Fukunaga et al. | |
| 5,983,896 | A * | 11/1999 | Fukunaga et al. | 128/207.14 |
| 6,129,082 | A | 10/2000 | Leagre | |
| 6,439,231 | B1 | 8/2002 | Fukunaga et al. | |
| 6,536,428 | B1 * | 3/2003 | Smith et al. | 128/203.17 |
| 6,564,799 | B1 * | 5/2003 | Fukunaga et al. | 128/205.29 |
| 6,733,556 | B1 * | 5/2004 | Luigi | 55/385.1 |
| 6,769,431 | B1 * | 8/2004 | Smith et al. | 128/203.16 |
| 6,874,500 | B1 * | 4/2005 | Fukunaga et al. | 128/204.18 |
| 2003/0111077 | A1 * | 6/2003 | Hooser et al. | 128/203.16 |
| 2003/0188746 | A1 | 10/2003 | Daugherty | |

FOREIGN PATENT DOCUMENTS

| | | |
|---|---|---|
| GB | 2025239 | 1/1980 |
| WO | WO 99/12598 | 3/1999 |

* cited by examiner

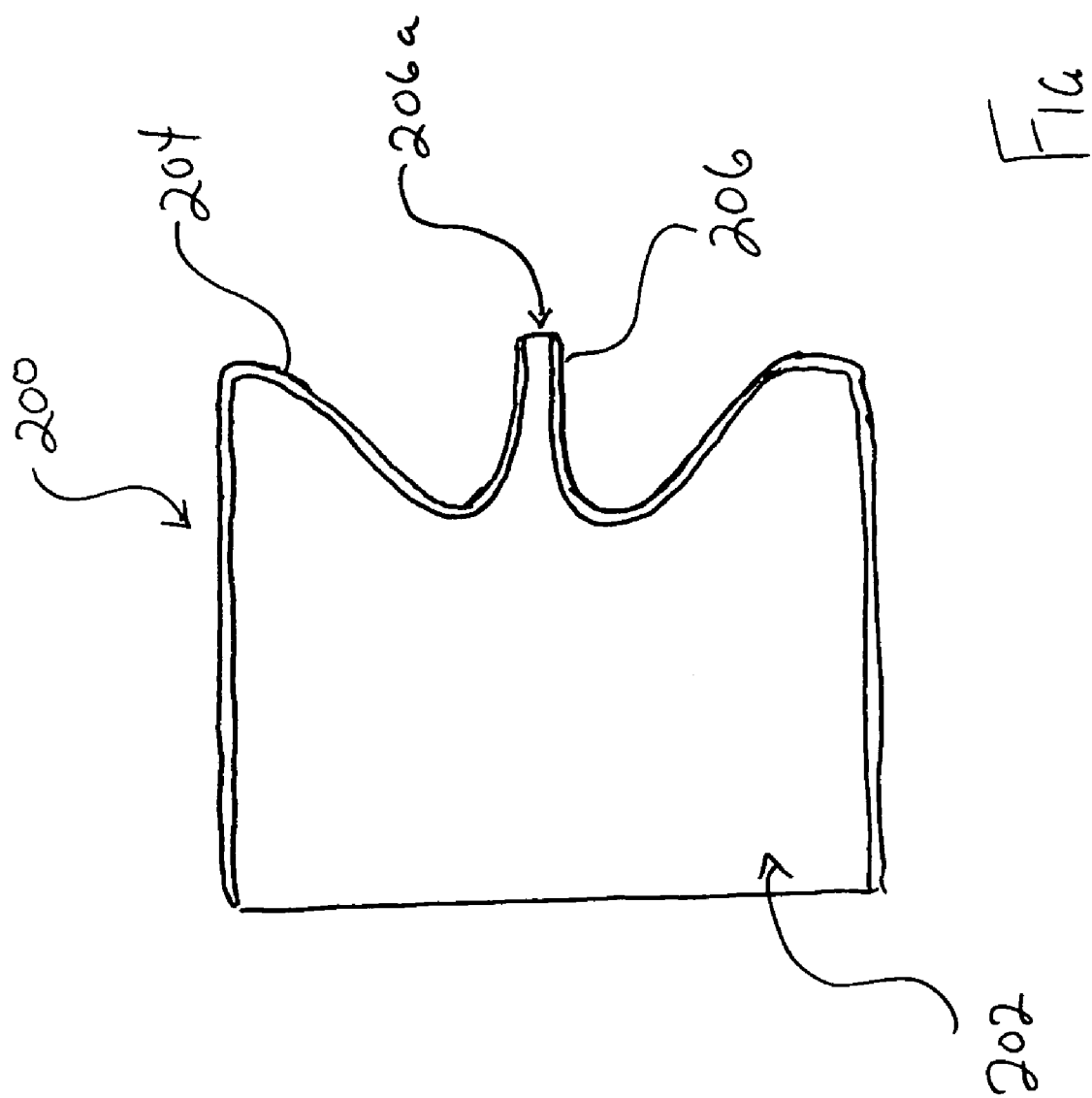

APPARATUS AND METHOD FOR HUMIDIFICATION OF INSPIRED GASES

CROSS-REFERENCE AND PRIORITY CLAIM TO RELATED APPLICATIONS

To the fullest extent permitted by law, the present continuation-in-part application claims priority to and the full benefit of nonprovisional patent application entitled "Apparatus and Method For Humidification of Inspired Gases", filed on May 13, 2003, having assigned Ser. No. 10/436,535.

TECHNICAL FIELD

The present invention relates generally to artificial ventilation systems, and more specifically to an apparatus and method for humidification of inspired gases, wherein the present invention is particularly suitable for, although not strictly limited to, the administration of humidified oxygen gas to patients recovering in a post-anesthesia care unit of a medical facility.

BACKGROUND OF THE INVENTION

Breathing circuits are commonly utilized in the operating room of a medical facility to convey anesthesia or inspiratory gases from an anesthesia machine to a patient, and to route expiratory gases from the patient to the anesthesia machine for subsequent cleansing and processing of same.

At present, several varieties of breathing circuits are available. One type of breathing circuit of substantial prevalence, and of particular relevance to the present invention as described herein, is a unilimb breathing circuit, wherein examples of such unilimb breathing circuits may be seen with reference to U.S. Pat. No. 4,265,235 to Fukunaga, U.S. Pat. No. 5,404,873 to Leagre et al., and U.S. Pat. No. 6,439,231 to Fukunaga et al. Generally, and as disclosed in the aforementioned patents, unilimb breathing circuits typically comprise a corrugated outer expiratory tube coaxially arranged about a corrugated inner inspiratory tube; that is, a tube-within-a-tube configuration. As such, one end of the unilimb breathing circuit, commonly referred to as the patient end, receives a connector for adapting the unilimb breathing circuit to a face mask, endotracheal tube, or laryngeal tube connected to the patient. The opposing end of the unilimb breathing circuit, commonly referred to as the machine end, typically receives a manifold for adapting the unilimb breathing circuit to an anesthesia machine for requisite inspiratory and expiratory gas manipulation.

Specifically, the manifold functions to direct anesthetic inspiratory gases from the anesthesia machine through the inner inspiratory tube for subsequent patient inhalation. During patient exhalation, expiratory gases flow through the outer expiratory tube and are redirected by the manifold to a carbon dioxide absorber of the anesthesia machine for subsequent removal of carbon dioxide gases therefrom. The cleansed exhaled gases may then be routed back through the inspiratory tube for rebreathing by the patient in conjunction with freshly administered anesthetic inspiratory gases.

In addition to the ability of unilimb breathing circuits to effectively bi-directionally conduct inspiratory and expiratory gases, unilimb breathing circuits are further capable of warming inherently lower temperature anesthesia gases. Essentially, patient expired gases flowing through the outer expiratory tube warm the inherently cooler anesthesia gases flowing through the inner inspiratory tube.

However, as a result of the temperature differential between the inspiratory and expiratory gases, moisture carried within the expiratory gases begins to condense within the corrugations of the expiratory tube, resulting in significant accumulation of moisture therewithin. Although such moisture may provide the ancillary benefit of humidifying the upper respiratory track of the patient during inspiration of dry anesthetic inspiratory gases, the moisture-laden unilimb breathing circuit is typically discarded after its first use, as medical practitioners have been unable to devise a secondary application for the moisture accumulated therewithin.

Discarding the breathing circuit presents the obvious ramification of excess waste of medical supplies, especially in view of the number of medical procedures requiring administration of anesthesia gases, and thus, the use of breathing circuits. Unfortunately, the cost of such expensive medical supplies is often imparted to the patient, adding to an often already overwhelming medical bill.

However, excess use and waste of medical supplies is not limited to disposal of the breathing circuits alone. Following completion of an operation or similar procedure requiring the administration of anesthesia gases via the breathing circuit, the patient is then typically transported from the operating room to the post-anesthesia care unit (i.e., PACU), where the patient is administered fresh oxygen gas to counteract the sedative effects of the anesthesia gases. Prior to patient inhalation of the oxygen gas, however, the inherently dry oxygen gas, delivered via a central oxygen source, must first pass through a bottle of sterile water for purposes of humidifying same, wherein the oxygen gas flow rate is regulated via a conventional flow meter. The humidified oxygen gas is then conveyed to the patient via a second, new length of tubing (i.e., corrugated tubing) connected to a conventional face tent worn by the patient.

Although the above-referenced method provides for the requisite humidification of oxygen gas, it possesses inherent disadvantages that make its implementation highly inefficient and uneconomical. More specifically, the patient is now further responsible for payment of the additional corrugated tubing, the bottle of sterile water, and the associated nebulizer adapter, typically utilized to atomize inspiratory gases passing therethrough. Furthermore, because the oxygen gas must first be passed through the gas-permeable "barrier" of sterile water for humidification purposes (i.e., bottle of sterile water), a higher quantity or percentage of oxygen gas must be passed into the bottle of sterile water to yield an overall effective percentage of humidified oxygen gas suitable for patient inhalation. As such, the patient is also responsible for payment of seemingly unavoidable excess quantities of oxygen gas.

Additionally, in view of efforts to develop products and/or processes that materially contribute to the environmental restoration and/or maintenance of basic life-sustaining natural elements, and the more efficient utilization and conservation of energy resources, the above-discussed method of oxygen gas humidification significantly hinders such present environmental conservation efforts. Specifically, because the bottle of sterile water, corrugated tubing, nebulizer, and associated adaptors and/or accessories, are discarded after first use, millions of gallons of precious water, and valuable petroleum resources utilized to manufacture the plastic tubing, bottle, nebulizer, and the like, are consumed to ensure the sustained provision of such medical supplies.

Therefore, it is readily apparent that there is a need for an apparatus and method for humidification of inspired gases, wherein said apparatus and method utilizes condensed expiratory gases deposited within a breathing circuit to humidify oxygen gas for subsequent patient inhalation, and wherein said apparatus and method functions to effectively eliminate dependency upon prior art methods of humidification, wasteful utilization of bottles of sterile water, corrugated tubing, nebulizer adapters and excess consumption of oxygen gas; thus, effectuating a cost savings for the patient and contributing to overall environmental conservation efforts.

BRIEF SUMMARY OF THE INVENTION

Briefly described, in a preferred embodiment, the present invention overcomes the above-mentioned disadvantages and meets the recognized need for such a device by providing an apparatus and method for humidification of inspired gases, wherein the present invention utilizes condensed expiratory gases deposited within the outer expiratory tube of a conventional unilimb breathing circuit to humidify oxygen gas (i.e., or any other inspiratory gas) for subsequent patient inhalation, and wherein the oxygen gas is now directed through the outer expiratory tube via a novel reverse flow adapter coupled to an oxygen gas source. The present invention preferably functions to effectively eliminate prior art methods of oxygen gas humidification that depend upon the wasteful utilization of bottles of sterile water, corrugated tubing, nebulizer adapters and excess consumption of oxygen gas; thus, effectuating a cost savings for the patient and contributing to overall environmental conservation efforts.

According to its major aspects and broadly stated, the present invention in its preferred form is an apparatus and method for humidification of inspired gases comprising a reverse flow adapter, a unilimb breathing circuit and face tent.

More specifically, the present invention is an apparatus and method for humidification of inspired gases, wherein the same unilimb breathing circuit utilized to deliver anesthesia gases to a patient in the operating room, is now also utilized to administer humidified oxygen to the same patient transported to and recovering in the PACU, thereby eliminating conventional use of a separate corrugated tubing, bottle of sterile water and nebulizer adapter.

As addressed earlier, during administration of anesthesia gases to the patient in the operating room or the like, patient expired gases flowing through the outer expiratory tube warm the inherently cooler anesthesia gases flowing through the inner inspiratory tube of the unilimb breathing circuit. As a result of the temperature differential between the inspiratory and expiratory gases, moisture carried within the expiratory gases begins to condense within the corrugations of the expiratory tube, resulting in accumulation of moisture therewithin.

Preferably, the accumulated moisture within the expiratory tube is now utilized to humidify the oxygen gas administered to the patient in the PACU; thus eliminating conventional use of a bottle of sterile water and related accessories.

Preferably, the unilimb breathing circuit utilized for the patient within the operating room now travels with the patient to the PACU, where it is coupled to a central oxygen source via a novel reverse flow adapter. The reverse flow adapter of the present invention permits fresh oxygen gas to now travel through the outer expiratory tube of the unilimb breathing circuit (i.e., concentrically about the outside of the inner inspiratory tube), wherein the oxygen gas interacts with the condensed expiratory gases therewithin, picking up moisture therefrom and becoming humidified. Preferably, the inner inspiratory tube is also completely shunted by way of the present novel reverse flow adapter; thereby, strategically directing oxygen gas through the outer expiratory tube for maximum interaction with the condensed expiratory gases therein.

Preferably, by eliminating conventional use of a bottle of sterile water and associated accessories for oxygen gas humidification, and by strategically directing oxygen gas flow through the expiratory tube for maximum interaction with condensed expiratory gases therewithin, a lower quantity of oxygen gas (i.e., as drawn from a central oxygen source) can be utilized to deliver an effective percentage of humidified oxygen gas suitable for patient inhalation.

Preferably, the present invention also contemplates eliminating use of conventional face tents utilized on patients for humidified oxygen gas inhalation. Currently, face tents possessing a standard 22 mm diametered male adapter are commonly utilized, wherein the 22 mm diametered male adapter is coupled to a piece of corrugated tubing having a slightly larger diametered opening to facilitate frictional engagement therewith. Preferably, the present invention contemplates the manufacture and use of a face tent having a 15 mm diametered male adapter for direct coupling of conventional unilimb breathing circuits thereto. Because most unilimb breathing circuits are commonly manufactured such that the outer expiratory tube possesses a connector or adapter having a diameter sufficient to frictionally engage a 15 mm male connector or adapter of a selected item, conventional corrugated tubing, and associated 22 mm male adapter face tents, utilized for humidified oxygen gas delivery can now be rendered largely extraneous in view of the present invention. However, it is recognized that any suitable face tent having any diametered male or female adapter could be cooperatively engaged to any unilimb breathing circuit having an opening or adapter with an accommodating diameter.

An alternate embodiment of the present invention contemplates the application of an alternate reverse flow adapter utilized to deliver humidified oxygen gas to intubated patients, yet permit the release of patient exhaled gases therethrough. Such an alternate reverse flow adapter advantageously eliminates the need for conventional application of T-pieces or T-tubes to intubated patients for purposes of providing an exit for exhaled or released gases.

Another alternate embodiment of the present invention contemplates the incorporation of a flow diluter with the reverse flow adapter, wherein the diluter would permit a clinician to dilute the percentage of oxygen gas being delivered to a patient (specifically, from 100% to 50%, or other selected percentages of dilution).

Still another alternate embodiment of the present invention contemplates the application of an intermediate adapter to assist in the delivery of oxygen gas to a patient when a breathing circuit is unavailable and/or was not utilized in the operating room, and therefore did not accompany the patient to the PACU. Such scenarios may arise when the patient is subjected to modified anesthesia control, wherein anesthesia is delivered intravenously, instead of through a facemask for subsequent inhalation (as a gas). The intermediate adapter would permit the reverse flow adapter to engage the connector and communicating tube of a standard nasal cannula assembly or simple facemask assembly.

Accordingly, a feature and advantage of the present invention is its ability to humidify oxygen gas via a novel and non-obvious apparatus and method.

A feature and advantage of the present invention is its novel reverse flow adapter.

A feature and advantage of the present invention is its ability to humidify oxygen gas via use of condensed water from expiratory gases that accumulate within the expiratory tube of a unilimb breathing circuit.

A feature and advantage of the present invention is its ability to effectively eliminate prior art methods of oxygen gas humidification that depend upon the wasteful utilization of bottles of sterile water, other corrugated tubing, nebulizer adapters and excess consumption of oxygen gas.

A feature and advantage of the present invention is its ability to materially contribute to the environmental restoration and/or maintenance of basic life-sustaining natural elements by eliminating the use of bottles of sterile water for oxygen gas humidification, thus effectively saving millions of gallons of water per year.

A feature and advantage of the present invention is its ability to materially contribute to the more efficient utilization and conservation of energy resources by conserving valuable petroleum resources that would otherwise be utilized to manufacture plastic corrugated tubing, plastic bottles for containing sterile water, and plastic nebulizer adapters, elements crucial to implementation of prior art methods of inspired gas humidification.

A feature and advantage of the present invention is its ability to effectuate a cost savings for the patient by reducing overuse of medical supplies.

A feature and advantage of the present invention is that the same unilimb breathing circuit utilized to deliver anesthesia gases to a patient in the operating room is now also utilized to administer humidified oxygen to the same patient transported to and recovering in the PACU.

A feature and advantage of the present invention is that, in comparison to prior art methods of oxygen gas humidification, a lower quantity of oxygen gas (i.e., as drawn from a central oxygen source) can now be utilized to deliver an effective percentage of humidified oxygen gas suitable for patient inhalation.

A feature and advantage of the present invention is its ability to be implemented with fewer connections and to reduce the likelihood of gas or liquid leaks as compared to prior art methods and devices.

A feature and advantage of the present invention is its ability to eliminate operational noises typically associated with conventional apparatuses and methods of gas humidification, wherein the whisper quite operation of the present invention assists clinicians in the accurate and noise-free assessment of breathing sounds or patterns relevant to a patient's clinical state of recovery.

A feature and advantage of the present invention is its ability to filter inspiratory oxygen gas and patient expiratory gases during delivery of humidified oxygen gas to a recovering patient, as opposed to filterless prior art apparatuses and methods of oxygen gas humidification and delivery.

These and other features and advantages of the present invention will become more apparent to one skilled in the art from the following description and claims when read in light of the accompanying drawings.

BRIEF DESCRIPTION OF THE DRAWINGS

The present invention will be better understood by reading the Detailed Description of the Preferred and Alternate Embodiments with reference to the accompanying drawing figures, in which like reference numerals denote similar structure and refer to like elements throughout, and in which.

DETAILED DESCRIPTION OF THE PREFERRED AND SELECTED ALTERNATE EMBODIMENTS

In describing the preferred and selected alternate embodiments of the present invention, as illustrated in FIGS. 1–7, specific terminology is employed for the sake of clarity. The invention, however, is not intended to be limited to the specific terminology so selected, and it is to be understood that each specific element includes all technical equivalents that operate in a similar manner to accomplish similar functions.

Figure 1:
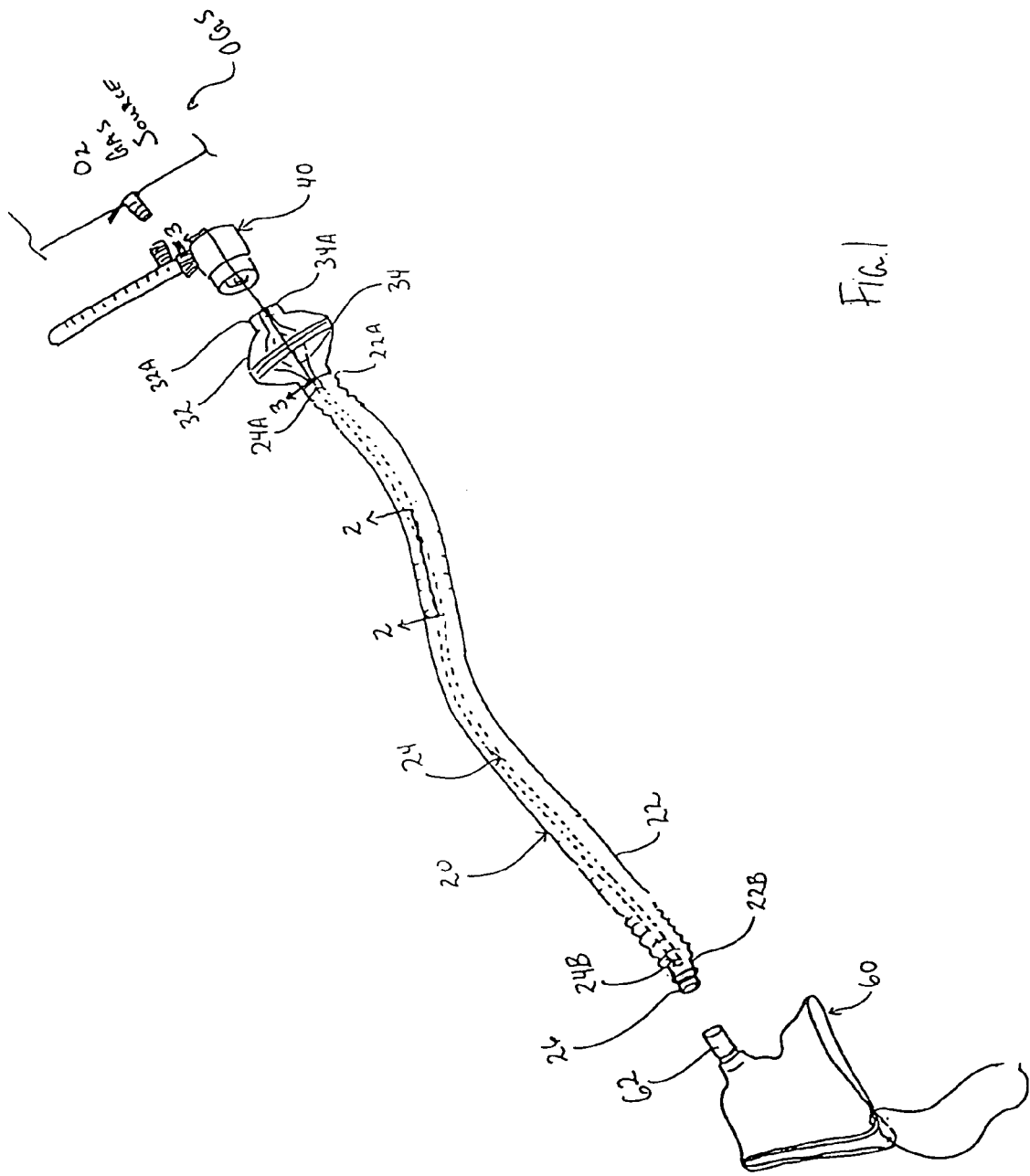
FIG. 1 is a perspective view of an apparatus for humidification of inspired gases according to a preferred embodiment of the present invention.
Figure 2:
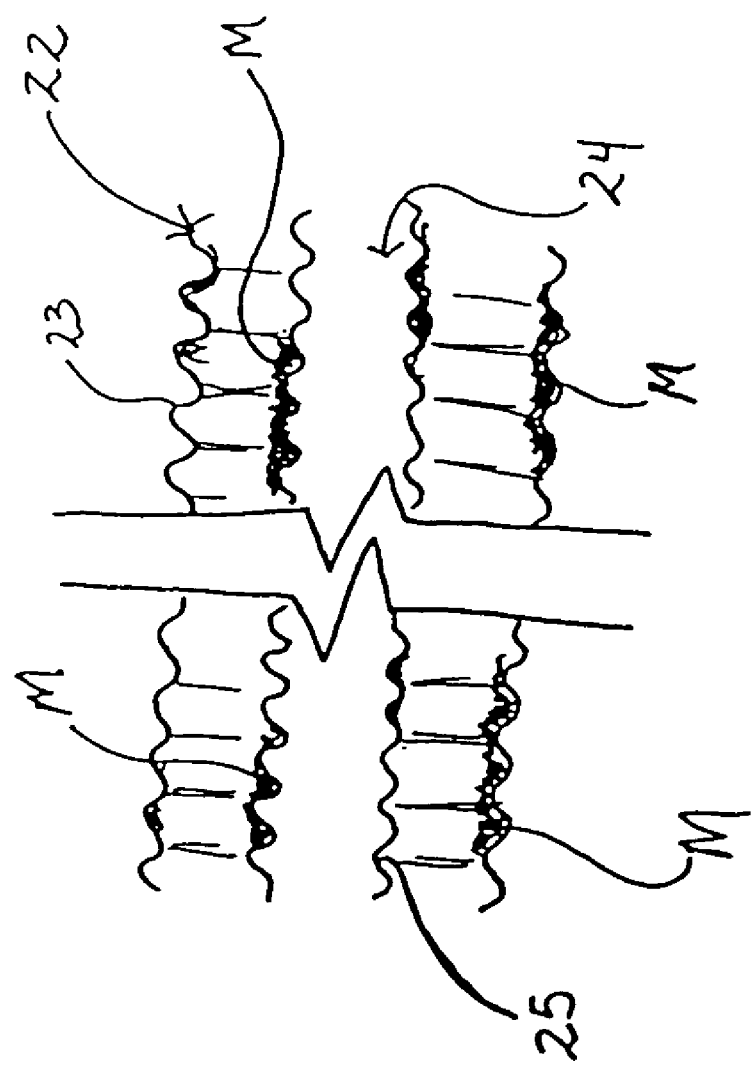
FIG. 2 is a cross-sectional view of FIG. 1 along section line 2—2.

Referring now to FIGS. 1–2, the present invention in a preferred embodiment is an apparatus 10, and associated method, for humidification of inspired gases, wherein apparatus 10 preferably generally comprises unilimb breathing circuit 20, reverse flow adapter 40 and face tent 60.

Specifically, unilimb breathing circuit 20 is preferably comparable to those disclosed in U.S. Pat. No. 4,265,235 to Fukunaga, U.S. Pat. No. 5,404,873 to Leagre et al., and U.S. Pat. No. 6,439,231 to Fukunaga et al. and, as such, is preferably utilized to administer anesthesia gases to a patient undergoing a surgical operation, or other medical procedure requiring patient sedation, and is further preferably utilized to convey expiratory gases away from the patient. Preferably, unilimb breathing circuit 20 possesses corrugated outer expiratory tube 22 coaxially arranged about corrugated inner inspiratory tube 24. Expiratory tube 22 preferably includes machine end 22A and patient end 22B, wherein inspiratory tube 24 also preferably includes machine end 24A and patient end 24B, respectively positioned proximal to ends 22A and 22B of expiratory tube 22.

Preferably, coaxial filter 30 is in fluid communication with machine ends 22A and 24A of expiratory tube 22 and inspiratory tube 24, respectively. More specifically, outer port 32 of coaxial filter 30 is in fluid communication with machine end 22A of expiratory tube 22, wherein inner port 34 is preferably in fluid communication with machine end 24A of inspiratory tube 22. As more fully described below, ends 32A and 34A of outer port 32 and inner port 34, respectively, preferably cooperatively engage reverse flow adapter 40 for implementation of the present method of humidification of inspired gas. As known within the art, coaxial filter 30 is preferably any suitable coaxial filter capable of being adapted to any conventional unilimb breathing circuit, and is preferably utilized to reduce and/or prevent bacterial transmission via suitable filter mediums such as, for exemplary purposes only, high efficiency particulate assembly (H.E.P.A.) filters.

Although unilimb breathing circuit 20, comparable to those disclosed in U.S. Pat. No. 4,265,235 to Fukunaga, U.S. Pat. No. 5,404,873 to Leagre et al., and U.S. Pat. No. 6,439,231 to Fukunaga et al., is preferably utilized to implement the present method of inspired gas humidification, it is contemplated in an alternate embodiment that other suitable breathing circuits could be utilized without departing from the appreciative scope of the present invention, so long as the selected breathing circuit contributes to the accumulation of condensed expiratory gases therewithin; such as, for exemplary purposes only, other types of unilimb breathing circuits, suitable dual-limb breathing circuits, filtered breathing circuits, unfiltered breathing circuits, corrugated breathing circuits and/or non-corrugated breathing circuits, wherein such alternate forms of breathing circuits are in full contemplation of the inventor in describing the present invention herein.

Preferably patient end 22B of expiratory tube 22 comprises connector 26 in communication therewith, wherein connector 26 is preferably appropriately dimensioned to facilitate frictional engagement of male adapter 62 of face tent 60 therewith, as more fully developed below.

Procedurally, and as known within the art, a patient undergoing a medical procedure requiring patient sedation is typically administered sedative or anesthetic gases via coupling of breathing circuit 20 to an anesthesia machine. Specifically, machine ends 22A and 22B of breathing circuit 20 receive a manifold (not shown) for adapting breathing circuit 20 to an anesthesia machine for requisite inspiratory and expiratory gas manipulation. Connector 26 of patient end 22B of expiratory tube 22 of breathing circuit 20 is coupled to an adapter (not shown) to facilitate engagement of a face mask, endotracheal tube, or laryngeal tube (not shown) thereto, wherein the face mask, or the like, is worn by the patient to facilitate inhalation of the anesthetic gases.

During such anesthetic gas administration to the patient, the patient's expired gases flow through expiratory tube 22 and warm the inherently cooler anesthesia gases flowing through inspiratory tube 24 of unilimb breathing circuit 20. As a result of the temperature differential between the inspiratory and expiratory gases, moisture carried within the patient's expiratory gases begins to condense within corrugations 23 of expiratory tube 22 and on the outer surface of corrugations 25 of inspiratory tube 24; thus, resulting in accumulation of moisture M therewithin, as best illustrated in FIG. 2. As more fully described below, the present method preferably utilizes moisture M and breathing circuit 20 to humidify the inherently dry oxygen gas (or other inspired gases) administered to the patient in the PACU; thereby, eliminating conventional use of a bottle of sterile water, corrugated tubing and nebulizer adapter.

Following completion of the medical procedure, and cessation of anesthesia gas administration, the patient is then typically (procedurally) transported from the operating room to the PACU, where the patient is administered fresh oxygen gas to counteract the sedative effects of the anesthesia gases. Generally, conventional methods of oxygen gas administration require the use of a new length or piece of corrugated tubing and a face tent (or endotracheal tube or laryngeal tube), because the moisture saturated (i.e., condensed expiratory gases) breathing circuit previously utilized for anesthesia gas administration has been discarded.

However, the present apparatus and method preferably seeks to utilize the moisture M saturated breathing circuit 20 to humidify the inherently dry oxygen gas (or other inspired gases) administered to the patient in the PACU; thereby, eliminating the conventional and uneconomical use of a bottle of sterile water, new corrugated tubing, and nebulizer adapter, for oxygen gas humidification.

Preferably, unilimb breathing circuit 20 and coaxial filter 30, along with accumulated moisture M still retained within expiratory tube 22, are transported with the patient to the PACU, wherein breathing circuit 20 is subsequently preferably coupled to a central oxygen gas source OGS via reverse flow adapter 40.

Figure 3:
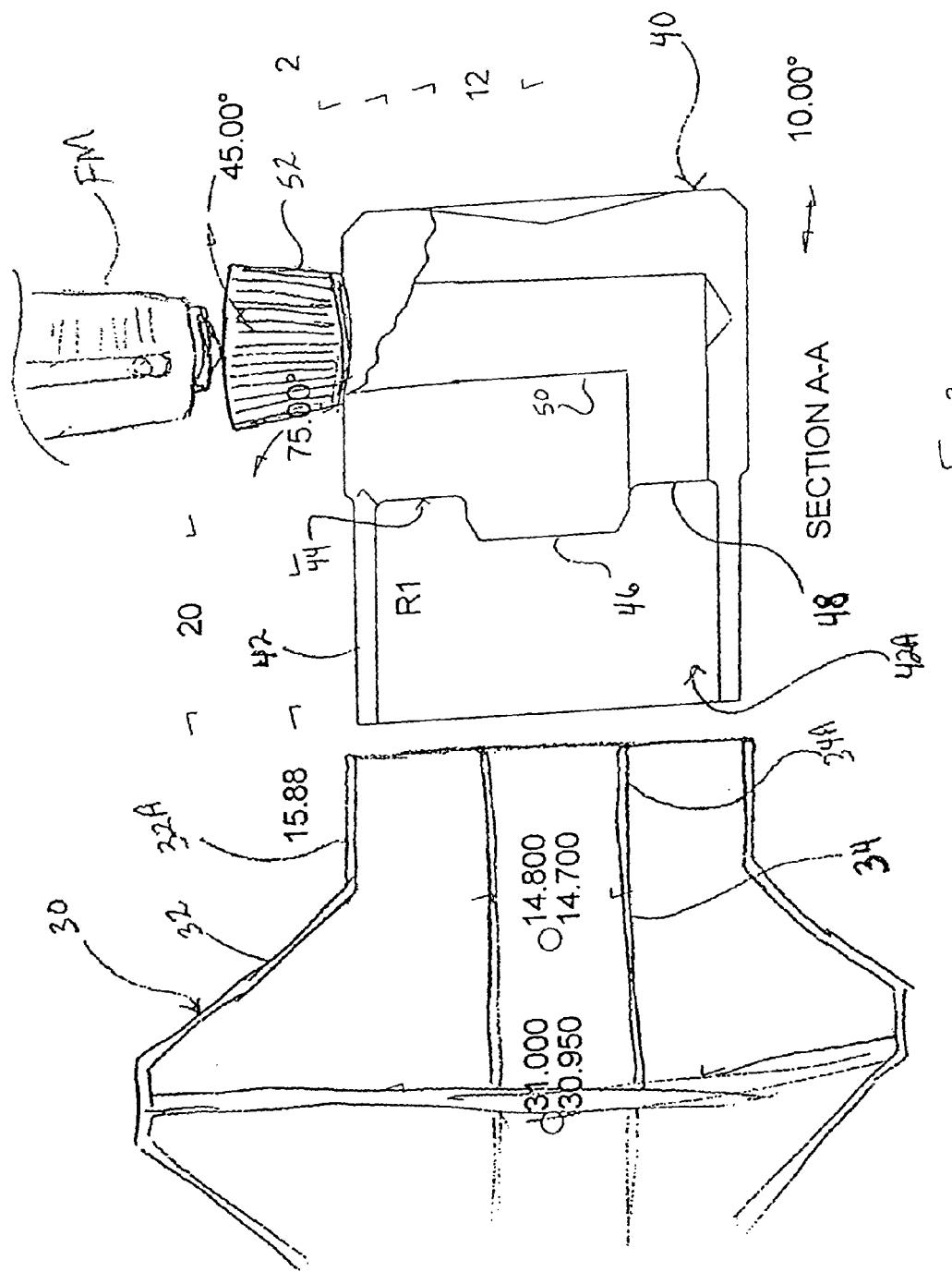
FIG. 3 is a partial cross-sectional view of f FIG. 1 along section line 3—3.

Referring now more specifically to FIG. 3, illustrated therein is a cross-sectional view of reverse flow adapter 40 and coaxial filter 30, wherein reverse flow adapter 40 preferably comprises an inlet 42 defining recessed area 42A. Inlet 42 preferably comprises a circumference sufficient to be frictionally received and engaged within end 32A of outer port 32 of coaxial filter 30. Preferably, centrally formed and extending outwardly from rear wall 44 of recessed area 42A is protuberance or stopper 46, wherein stopper 46 is preferably dimensioned to be frictionally received and engaged within end 34A of inner port 34 of coaxial filter 30, for purposes more fully described below.

Preferably formed through rear wall 44 of recessed area 42A is aperture 48, wherein aperture 48 is preferably in fluid communication with substantially L-shaped passageway or channel 50. Preferably, conventional flow meter FM is threadably coupled to, and brought into fluid communication with, channel 50 via coupler 52, as known within the art. Preferably, upon subsequent engagement of flow meter FM to central oxygen gas source OGS, and upon release of oxygen gas from gas source OGS, oxygen gas preferably flows therefrom, through flow meter FM, through channel 50, and thereafter, preferably exits aperture 48 for dispersion through expiratory tube 22.

More specifically, upon slidably engaging end 32A of outer port 32 of coaxial filter 30 over inlet 42 of reverse flow adapter 40, end 34A of inner port 34 of coaxial filter 30 preferably frictional receives and engages stopper 46 of reverse flow adapter 40, thus effectively shunting flow of gas therethrough. As such, upon flow of oxygen gas through aperture 48 of reverse flow adapter 40, as delivered via oxygen source OGS, a continuous stream of oxygen gas preferably momentarily circulates within recessed area 42A of reverse flow adaptor 40, and is thereafter preferably uniformly expelled through outer port 32 of coaxial filter 30, for subsequent uniform travel and distribution through communicating expiratory tube 22.

Preferably, as oxygen gas travels through expiratory tube 22 (i.e., on the outside of inspiratory tube 24) in a natural toroidal and/or helical manner toward patient end 22B thereof, the oxygen gas preferably interacts with accumulated moisture M (i.e., condensed expiratory gases) deposited within corrugations 23 of expiratory tube 22 and on the outer surface of corrugations 25 of inspiratory tube 24, picking up moisture therefrom and thus, becoming humidified. Preferably, via the shunting of end 34A of inner port 34 of coaxial filter 30 by stopper 46 of reverse flow adapter 40, inspiratory tube 24 is also effectively completely shunted; thus, strategically directing oxygen gas through expiratory tube 22 for maximum interaction with accumulated moisture M therewithin.

Preferably, when the oxygen gas traveling through expiratory tube 22 reaches patient end 22B thereof, the oxygen gas is preferably sufficiently humidified for patient inhalation, wherein the humidified oxygen gas preferably exits patient end 22B through a conventional connector 26.

Connector 26 preferably possesses an appropriately dimensioned diameter to facilitate frictional engagement of male adapter 62 of face tent 60 therewith. Preferably, male adapter 62 possesses a diameter of approximately 15 mm for the direct frictional coupling of connector 26 of unilimb breathing circuit 20 thereto, as connector 26 is typically (conventionally) manufactured to possess an inner diameter of approximately 15 mm. As stated earlier, because most unilimb breathing circuits are commonly manufactured such that the outer expiratory tube possesses a connector or adapter having a diameter sufficient to frictionally engage a 15 mm male connector or adapter of a selected item, conventional corrugated tubing, and associated 22 mm male adapter face tents, utilized for humidified oxygen gas delivery, can now be rendered largely extraneous in view of the present invention. However, it is recognized that any suitable face tent having any diametered male or female adapter could be cooperatively engaged to any unilimb breathing circuit having an opening or connector with an accommodating diameter, wherein such dimensions and/or configurations could be utilized without departing from the appreciate scope of the present invention, and are in full contemplation of the inventor in describing the present invention herein.

Preferably, by eliminating conventional use of a bottle of sterile water and associated accessories for oxygen gas humidification, and by strategically directing oxygen gas flow through expiratory tube 22 for maximum interaction with accumulated moisture M therewithin, a lower quantity of oxygen gas (i.e., as drawn from central oxygen gas source OGS) can be utilized to deliver an effective percentage of humidified oxygen gas suitable for patient inhalation. Specifically, conventional methods of oxygen gas humidification utilizing a bottle of sterile water for humidification purposes, typically require that the central oxygen gas source OGS maintain an oxygen flow rate of 10 to 12 liters per minute. However, via implementation of the present method of oxygen gas humidification, oxygen flow rates can effectively be reduced to 5 to 6 liters per minute. Additionally, clinical studies and experimental testing conducted by the inventor have established that implementation of the present method of oxygen gas humidification, utilizing an oxygen flow rate of 6 liters per minute, provides the requisite 98% to 100% inspired oxygen level (FiO2) for stabilization of patient blood oxygen saturation.

Although the present apparatus and method is preferably utilized for humidification of oxygen gas, it should be recognized that the present invention could be utilized to humidify any suitable gas and/or combination of gases.

Additionally, although the present method may be implemented with an oxygen flow rate of 6 liters per minute, it is contemplated in an alternate embodiment that either lower or higher oxygen flow rates could be utilized.

Figure 4:
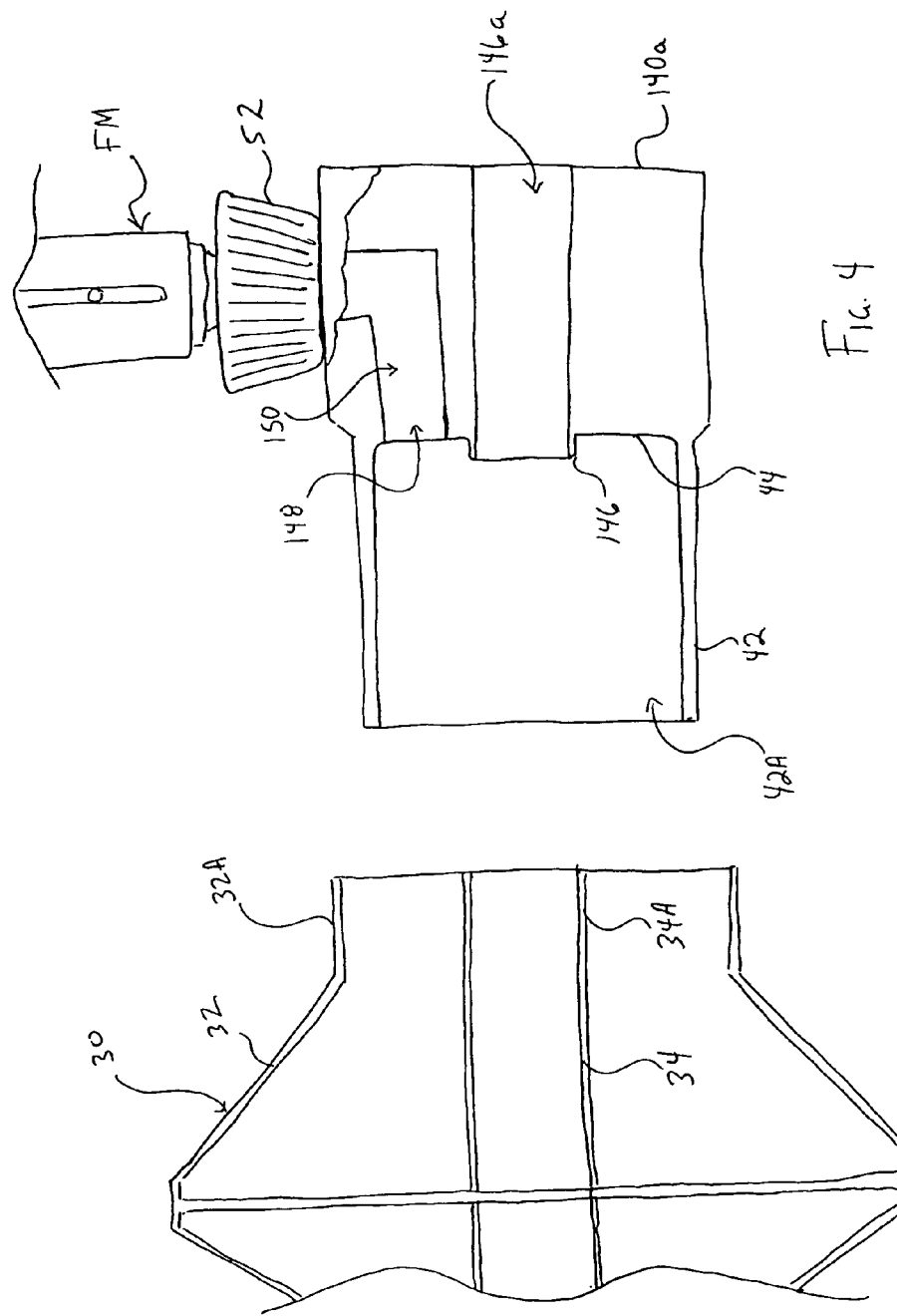
FIG. 4 is a cross-sectional view of a reverse flow adapter according to an alternate embodiment of the present invention.

Referring now more specifically to FIG. 4, illustrated therein is an alternate embodiment of apparatus 10, wherein the alternate embodiment of FIG. 4 is substantially equivalent in form and function to that of the preferred embodiment detailed and illustrated in FIGS. 1–3 except as hereinafter specifically referenced. Specifically, the embodiment of FIG. 4 replaces reverse flow adapter 40 with reverse flow adapter 140, wherein adapter 140 is utilized to deliver humidified oxygen gas to intubated patients, yet permit the release of patient exhaled gases therethrough. Similar to reverse flow adapter 40, adapter 140 comprises inlet 42 defining recessed area 42A, wherein inlet 42 comprises a circumference sufficient to be frictionally received and engaged within end 32A of outer port 32 of coaxial filter 30. Centrally formed and extending from rear wall 44 of recessed area 42A is hollowed protuberance 146, defining passageway 146A extending therethrough, and exiting out from anterior side 140a of adapter 140. Protuberance 146 is dimensioned to be frictionally received and engaged within end 34A of inner port 34 of coaxial filter 30, for purposes more fully described below.

Formed through rear wall 44 of recessed area 42A, and positioned above protuberance 146, is aperture 148, wherein aperture 148 is in fluid communication with substantially L-shaped passageway or channel 150. Aperture 148 and channel 150 are positioned above protuberance 146 so as to not cross-sect and interrupt passageway 146a, for purposes more fully described below. Functionally equivalent to channel 50 and aperture 48 of reverse flow adapter 40, channel 150 and aperture 148 function to permit flow of oxygen gas therethrough, as delivered via conventional flow meter FM and central oxygen gas source OGS, for subsequent channeling of same through expiratory tube 22.

More specifically, upon slidably engaging end 32A of outer port 32 of coaxial filter 30 over inlet 42 of reverse flow adapter 140, end 34A of inner port 34 of coaxial filter 30 frictional receives and engages protuberance 146 of reverse flow adapter 140, thus bringing passageway 146a thereof in fluid communication with inner port 34 and communicating inspiratory tube 24. As described above, oxygen gas delivered via central oxygen gas source OGS, flows through aperture 148 of reverse flow adapter 140, through outer port 32 of coaxial filter 30, and through expiratory tube 22, for subsequent interaction with, and humidification by, moisture M accumulated therewithin.

To facilitate delivery of such humidified oxygen gas to intubated patients (i.e., patients fitted with an endotracheal tube or laryngeal tube), connector 26 engaged with patient end 22B of expiratory tube 22 is connected to a conventional adapter formed at the end of the endotracheal tube or laryngeal tube extending out from the intubated patient, thereby permitting the flow of humidified oxygen gas therethrough.

However, as the natural process of inhalation necessitates subsequent exhalation, intubated patients inhaling or receiving oxygen gas must be supplied with a method or avenue to exhale waste gases. Conventional practice requires the attachment of a T-tube or T-piece to the end of the endotracheal tube or laryngeal tube extending out from the patient, wherein a tube carrying oxygen gas may be connected to a first arm thereof. As such, and as known within the art, when an intubated patient exhales, the exhaled gases exit through a second arm of the T-piece, while fresh oxygen gas continues to enter through the first arm thereof.

However, utilization of reverse flow adapter 140 with unilimb breathing circuit 20 for application to intubated patients advantageously eliminates the need for T-pieces, or the like. Specifically, because passageway 146a of protuberance 146 is in fluid communication with inner port 34 of coaxial filter 30 and communicating inspiratory tube 24, exhaled gases released by an intubated patient travel through inspiratory tube 24, through inner port 34 of coaxial filter 30, through passageway 146a of protuberance 146, and exit through anterior side 140a of reverse flow adapter 140; while humidified oxygen gas continues to flow through expiratory tube 22 and through a connecting endotracheal or laryngeal tube. It is contemplated in an alternate embodiment that a face tent could be connected to expiratory tube 22 for utilization of reverse flow adapter 140 with non-intubated patients.

Figure 5:
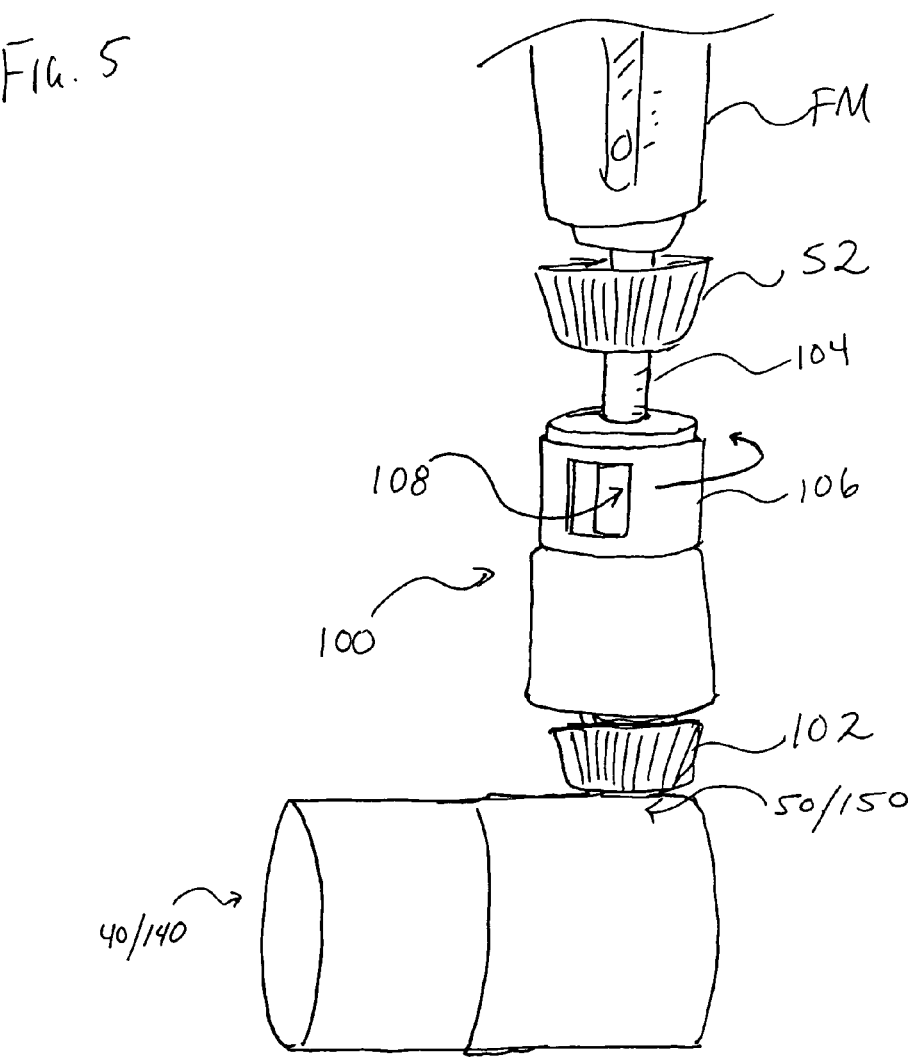
FIG. 5 is a perspective view of a combination flow diluter and reverse flow adapter according to an alternate embodiment of the present invention.

Referring now more specifically to FIG. 5, illustrated therein is an alternate embodiment of apparatus 10, wherein the alternate embodiment of FIG. 5 is substantially equivalent in form and function to that of the preferred embodiment detailed and illustrated in FIGS. 1–3 except as hereinafter specifically referenced. Specifically, the embodiment of FIG. 5 incorporates flow diluter 100, wherein flow diluter 100 is utilized to ween a patient off oxygen gas as the patient's normal metabolic functions return, and as the sedative effects of anesthesia gases steadily diminish, and wherein such flow diluters are known within the art. Specifically, diluter 100 comprises lower coupler 102, threadably engageable with channels 50 or 150 of selected adapter 40 or 140, respectively. Upper connecter 104 of flow diluter 100 is adapted to be threadably engaged with coupler 52 of conventional flow meter FM; although integral formation of each component is readily recognized as an alternate embodiment. As such, oxygen gas, as delivered via central oxygen gas source OGS, travels through flow meter FM, through flow diluter 100, and through selected adapter 40 or 140. To dilute the percentage of oxygen gas being delivered to a patient (specifically, from 100% to 50%), a rotatable sleeve 106 disposed on diluter 100 is rotated to expose aperture 108 formed through diluter 100, wherein room air is permitted to enter therethrough, intermix with the metered oxygen gas flowing therethrough (i.e., via a Venturi effect), and dilute the final inhaled and humidified oxygen gas from 100% to 50%. It should be recognized that diluter 100 and associated sleeve 106 and aperture 108 could be modified to permit dilution of oxygen gas to any desired percentage, ranging from 0% to 100%.

Figure 6:
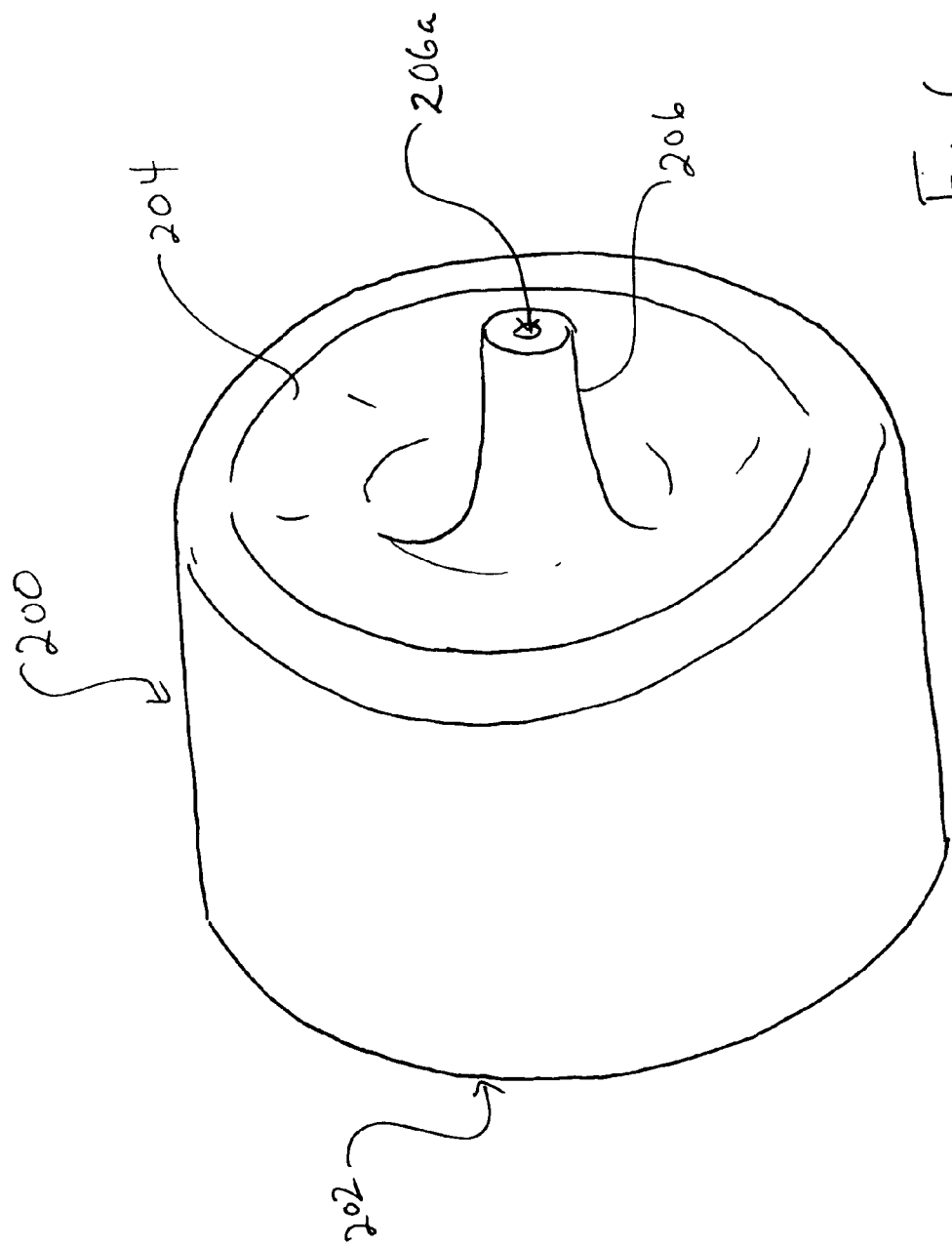
FIG. 6 is a perspective view of an intermediate adapter for application to a reverse flow adapter of the preferred or alternate embodiment of the present invention; and, FIG. 7 is a cross-sectional view of an intermediate adapter for application to a reverse flow adapter of the preferred or alternate embodiment of the present invention.

Referring now more specifically to FIGS. 6–7, illustrated therein is intermediate adapter 200, wherein intermediate adapter 200 is utilized to assist in the delivery of oxygen gas to a patient when breathing circuit 20 is unavailable and/or was not utilized in the operating room, and therefore did not accompany the patient to the PACU. Such scenarios may arise when the patient is subjected to modified anesthesia control, wherein anesthesia is delivered intravenously, instead of through a facemask for subsequent inhalation (as a gas). Intermediate adapter 200 is substantially cap-like, comprising recessed area 202, closed top side 204, and nipple 206 extending from top side 204, wherein nipple 206 comprises passageway 206a formed therethrough for the exit of oxygen gas or other inspiratory gases therefrom. Recessed area 202 of intermediate adapter 200 is dimensioned to engage and frictionally receive inlet 42 of selected reverse flow adapter 40 or 140. Nipple 206 is dimensioned to be received by conventional connectors formed at the end of standard nasal cannula assemblies and/or simple facemask assemblies. As such, oxygen gas as delivered via central oxygen gas source OGS though flow meter PM, and thereafter, through selected adapter 40 or 140, is channeled through passageway 206a of and nipple 206, and then through the connector and communicating tube of the standard nasal cannula assembly or simple facemask assembly. It is contemplated that diluter 100 could be incorporated with such an assembly.

It is contemplated in another alternate embodiment that, although reverse flow adapter 40 possesses aperture 48 alone, reverse flow adapter 40 could possess any number of apertures for expelling oxygen gas through expiratory tube 22, wherein the aperture(s) could be selectively positioned within reverse flow adapter 40. Adapter 140 may also be similarly modified.

It is contemplated in yet another alternate embodiment that reverse flow adapter 40 could possess a plurality of apertures concentrically arranged about stopper 46 for expelling oxygen gas through expiratory tube 22. Adapter 140 may also be similarly modified.

It is contemplated in yet another alternate embodiment that reverse flow adapters 40 and/or 140 could be integrally formed with a conventional flow meter FM so as to eliminate the need to threadably engage adapters 40 and 140 thereto via coupler 52. Such an embodiment could further have diluter 100 integrally formed therewith.

It is contemplated in still another alternate embodiment that coaxial filter 30 could be entirely eliminated, wherein machine ends 22A and 24A of expiratory tube 22 and inspiratory tube 24, respectively, would be directly coupled to reverse flow adapters 40 or 140.

It is contemplated in still another alternate embodiment that stopper 46 of reverse flow adaptor 40 could be entirely eliminated; thus, permitting oxygen gas to flow through both expiratory tube 22 and inspiratory tube 24.

It is contemplated that the present apparatus and method could be implemented during the transport of a patient from one location to another via utilization of a mobile oxygen gas source.

It is contemplated in still another alternate embodiment that other suitable face tents, masks, cannula, tubing, and/or the like could be adapted to the patient for effective inhalation of humidified inspired gases.

It is contemplated in still another alternate embodiment that reverse flow adapters 40 or 140 and flow meter FM could be integrally formed and/or permanently mounted to central oxygen gas source OGS, as each coaxial filter 30 of each unilimb breathing circuit 20 would prevent bacterial or microbial contamination of reverse flow adaptors 40 or 140 and/or flow meter FM.

It is contemplated in still another alternate embodiment that ends 32A and 34A of outer port 32 and inner port 34 of coaxial filter 30 could be frictionally received and engaged by reverse flow adapters 40 or 140.

It is contemplated in still another alternate embodiment that small quantities of sterile water could be introduced into expiratory tube before or during administration of oxygen gas (or other inspired gases) for purposes of maintaining a select quantity of moisture therein.

Having thus described exemplary embodiments of the present invention, it should be noted by those skilled in the art that the within disclosures are exemplary only, and that various other alternatives, adaptations, and modifications may be made within the scope of the present invention. Accordingly, the present invention is not limited to the specific embodiments illustrated herein, but is limited only by the following claims.

What is claimed is:

1. An apparatus for reversing flow of inspiratory gas through a unilimb breathing circuit for humidification of the inspiratory gas, said apparatus comprising:

a reverse flow adapter comprising a venting aperture, said reverse flow adapter adapted to be coupled to an inner tube and an outer tube of the unilimb breathing circuit, wherein the inspiratory gas flows through said reverse flow adapter and subsequently through the outer tube of the unilimb breathing circuit, and wherein said venting aperture is in fluid communication with the inner tube of the unilimb breathing circuit;

wherein the outer tube retains moisture deposited therein via condensation of moisture from patient expiratory gases;

wherein said reverse flow adapter is adapted to be coupled to a conventional inspiratory gas source; and, wherein inspiratory gas flows from the conventional inspiratory gas source, through said reverse flow adapter, through the outer tube, and subsequently interacts with and is humidified by said moisture condensed within the outer tube, thereby creating a humidified inspiratory gas for patient inhalation.

2. The apparatus of claim 1, wherein the outer tube is coaxially disposed about the inner tube of the unilimb breathing circuit.

3. The apparatus of claim 1, wherein a face tent coupled to the outer tube is worn by the patient during inhalation of said humidified inspiratory gas.

4. The apparatus of claim 3, wherein patient exhaled gas flows through the inner tube of the unilimb breathing circuit, through said reverse flow adapter, and exits from said venting aperture of said reverse flow adapter.

5. The apparatus of claim 1, wherein said moisture is deposited within the unilimb breathing circuit via condensation of patient expiratory gases released or expelled by a sedated patient undergoing a medical procedure requiring administration of anesthesia or other inspiratory gases to the patient during performance of the medical procedure.

6. The apparatus of claim 5, wherein the unilimb breathing circuit utilized to administer anesthesia or other inspiratory gases to the patient during performance of the medical procedure is thereafter utilized to convey and humidify subsequently administered oxygen gas or other inspiratory gas delivered to the patient recovering from sedative effects of the inspiratory gases administered during performance of the medical procedure, the subsequently administered gas humidified via said moisture accumulated within the outer tube of the unilimb breathing circuit via condensation of the patient expiratory gases previously released by the sedated patient.

7. The apparatus of claim 1, wherein the unilimb breathing circuit is equipped with a coaxial filter in fluid communication with the outer tube and the inner tube.

8. The apparatus of claim 1, further comprising a flow diluter.

9. The apparatus of claim 1, further comprising an intermediate adapter dimensioned to engage said reverse flow adapter, said intermediate adapter comprising a nipple, said nipple comprising a passageway formed therethrough for the exit of inspiratory gases therefrom, wherein said nipple is dimensioned to be received by a connector formed on a nasal cannula assembly or a simple facemask assembly.

10. An apparatus for reversing flow of inspiratory gas through a unilimb breathing circuit for humidification of the inspiratory gas, said apparatus comprising:

a reverse flow adapter comprising a venting aperture, said reverse flow adapter adapted to be coupled to the unilimb breathing circuit, wherein said reverse flow adapter comprises an inlet, said venting aperture formed through said inlet, and wherein said inlet further comprises a flow aperture for permitting inspiratory gases flowing from a central inspiratory gas source to flow therethrough and pass through said inlet;

wherein said inlet is adapted to be coupled to an outer expiratory tube of the unilimb breathing circuit, resulting in said flow aperture being in fluid communication with an inner space of the outer expiratory tube, and wherein said venting aperture is in fluid communication with an inner space of an inner inspiratory tube of the unilimb breathing circuit;

wherein inspiratory gases flowing from a central inspiratory gas source flow through said flow aperture of said reverse flow adapter, into said inlet of said reverse flow adapter, and through the inner space of the outer expiratory tube; and, wherein the inspiratory gases flowing through the outer expiratory tube interact with and are humidified by moisture from condensed expiratory gases deposited therein during a patient's prior exhalation, thereby creating a humidified inspiratory gas for patient inhalation.

11. The apparatus of claim 10, wherein patient exhaled gas flows through the inner inspiratory tube of the unilimb breathing circuit and exits from said venting aperture of said reverse flow adapter.

* * * * *